United States Patent
Zimmerman

(10) Patent No.: US 6,905,487 B2
(45) Date of Patent: Jun. 14, 2005

(54) DERMAL TREATMENT APPLICATOR AND METHOD RELATING THERETO

(76) Inventor: Maryann B. Zimmerman, 5296 Bagpipers La., Virginia Beach, VA (US) 23464

( * ) Notice: Subject to any disclaimer, the term of this patent is extended or adjusted under 35 U.S.C. 154(b) by 208 days.

(21) Appl. No.: 10/228,445

(22) Filed: Aug. 27, 2002

(65) Prior Publication Data

US 2003/0056276 A1 Mar. 27, 2003

Related U.S. Application Data

(60) Provisional application No. 60/315,108, filed on Aug. 27, 2001.

(51) Int. Cl.$^7$ .................. A61M 35/00; A41D 19/00
(52) U.S. Cl. ................. 604/292; 2/164; 2/167
(58) Field of Search .................. 2/164, 167, 161.7; 604/292

(56) References Cited

U.S. PATENT DOCUMENTS

| | | | | |
|---|---|---|---|---|
| 2,501,565 A | * | 3/1950 | Halley | 604/292 |
| 4,087,675 A | * | 5/1978 | Sansonetti | 604/292 |
| 5,614,202 A | * | 3/1997 | DeFina | 424/402 |
| 5,891,116 A | * | 4/1999 | Mast | 604/290 |
| 6,117,119 A | * | 9/2000 | Gould | 604/290 |
| 6,197,305 B1 | * | 3/2001 | Friedman et al. | 424/737 |
| 6,673,054 B1 | * | 1/2004 | Gould et al. | 604/292 |

OTHER PUBLICATIONS

Worwood, Valeria Ann, The Complete Book of Essential Oils & Aromatherapy, pp. 152–154, published by New World Library, Nevada, California USA—Copyright 1991.

* cited by examiner

*Primary Examiner*—Larry I. Schwartz
*Assistant Examiner*—Linh Truong
(74) *Attorney, Agent, or Firm*—Goldizen & Associates; Bradley D. Goldizen

(57) ABSTRACT

A manicure/pedicure glove for treatment of damaged skin areas and/or enhancing nail growth is presented. The glove comprises a single layer of breathable material having a second layer of material in a particular treatment area. The second layer of material is impregnated with a wax-based preparation and may or may not be separated from the external layer in the treatment area by a thin plastic film or exterior coating to ensure non-leakage. Alternatively, the glove may only cover the finger or toe tip. In use, the glove is provided. A hand or foot is inserted into the glove and the glove worn for a sufficient period to permit the wax-based preparation to penetrate into the treatment area. The glove is then removed and may be disposed or, or alternatively may be used for a specified number of repeated applications.

14 Claims, 5 Drawing Sheets

DERMAL TREATMENT APPLICATOR AND METHOD RELATING THERETO

This application claims priority from U.S. Provisional Patent Application Ser. No. 60/315,108 filed on Aug. 27, 2001.

This application did not receive federal funding.

FIELD OF THE INVENTION

The present invention relates generally to cosmetic applicators or applicators for applying a dermal treatment to damaged skin. More particularly, the invention relates to a method and applicator used for treating areas of damaged skin areas on the limbs or extremities. It is further directed to a method for enhancing the growth of finger and/or toe nails.

BACKGROUND OF THE INVENTION

Women generally desire to have long and beautiful finger nails coupled with soft skin on the hands and feet. Often in fulfilling this desire, they will apply false nails, typically made of acrylic, to their natural nails and apply moisturizers to their skin. Application of false nails damages the finger nails. To avoid this damage and still have long nails, one must grow the nail naturally and refrain from using false nails. Likewise, moisturizers must be applied regularly to realize soft skin. These processes are time-consuming and may be difficult to achieve because time constraints as physical limitations such as weak and slow growing nails.

The cuticle, an outer layer of skin found at the base of nail, may also be easily damaged upon exposure to adverse environmental conditions such as the application of artificial nails; various cleaning compounds; and/or dry temperature environments. Once the cuticle has been damaged, pain, bleeding and infection may set-in. Therefore, it is desirable to keep the skin lubricated to avoid damage and/or to repair the damaged tissue.

Past remedies for the repair of nail and cuticle damage have included cuticle creams, gelatin capsules, lotions, and using various gloves or booties containing cream preparations. The problem with applying creams, capsules and lotions to the skin is that the preparation is applied only topically. However, for full healing and protection, deep penetration is necessary. Some have tried to solve this problem by designing gloves and booties that are capable to dispensing preparations to the hands and feet.

For example, Charos in U.S. Pat. No. 3,342,182 designed a packaged cream applicator that is a glove having a soft, absorbent inner side and a substantially impermeable outer side. The inner side or the lining is impregnated with a medical preparation such as a cosmetic cream. The device is sold to the consumer ready for use. The user dampens or moistens her hands and inserts them into the gloves and simply wears the impregnated gloves. By manipulating the hands and the fingers during ordinary activities, the packaged cream is mixed with the moisture in the skin and is dispensed evenly on the skin. The problem with this glove is that there is uneven distribution of the cream to the skin. Further, it does not include any concentration to a particular area of the hand or foot. Moreover, the impermeable outer layer restricts breathing by the skin and causes the hand or foot to sweat which may inhibit the skins ability to absorb the cosmetic cream.

Stager in U.S. Pat. No. 4,122,554; U.S. Pat. No. 4,185,330; and Canadian Patent No. 1,092,060 disclose a disposable cosmetic glove which is characterized by superposed first and second layers of lotion impervious material and an inner glove lining formed by superposed first and second lotion absorbent layers. The absorbent layers are uniformly impregnated with a cosmetic lotion. Alternatively, the user could apply the lotion to his or her hands first and then put the gloves on to saturate the inner lining prior to use. The shell and lining layers are sealed together along the marginal edge of the glove and a small amount of thermosetting adhesive is deposited at a number of selected locations around the marginal edge of the glove to anchor the liner as the glove is worn. The glove, although disposable, is layered such that the outer shell layer is a thermoplastic film of 1–2 mils thickness. The use of this film does not permit the glove to breathe and causes the hand to sweat. Thus, Stager suffers from similar problems mentioned above with respect to Charos. Additionally, another drawback to Stager is that the layered configuration is prone to de-lamination and may come apart while in use.

Schneiderman in U.S. Pat. No. 4,567,065 provides dispenser gloves and stockinets which may or may not contain the treating agent. In Schneiderman, the glove is prepared from vinyl-latex and has a hollow lumen into which a treating agent is placed prior to packaging. This design causes the hands to sweat. Therefore, Schneiderman suffers from the same problems as the previously mentioned patents.

DeFina, U.S. Pat. No. 5,614,202 discloses a moisturizing glove comprised of three layers. An exterior layer of non-porous material is formed on the top side of the middle layer. The middle layer is saturated with a lotion. An inner layer includes a plurality of pores formed on the bottom side of the middle layer. The inner layer creates a cavity for receiving and enveloping a human extremity such as a hand. Since the exterior layer of the DeFina glove is nonporous, it suffers from the same deficiencies mentioned above.

It is an object of the invention to provide a delivery system that can be readily used to apply a lubricating, moisturizing or medicinal agent to the epidermis of an individual.

It is another object of the invention to provide a delivery system that limits the lubricating, moisturizing or medicinal agent to a localized portion of the delivery system.

It is another object of the invention to provide a delivery system that will impart a cosmetic or medicinal agent to a skin surface for an extended period of time.

It is an object of the present invention to provide a single-layer disposable manicure/pedicure glove.

Another object of the present invention is to provide a manicure/pedicure glove that is breathable.

Another object of the present invention is to provide a manicure/pedicure glove that is pre-lubricated but does not leak.

Another object of the present invention is to provide a manicure/pedicure glove that contains a wax-based treatment that enhances the growth of finger and toe nails and/or heals and strengthens nails, cuticles, and softens rough skin.

SUMMARY OF THE INVENTION

The aforementioned objects and other objects of the invention were achieved by the present invention which is an applicator which may be a glove, a patch, stocking or sock.

In one embodiment, a manicure/pedicure glove comprising an exterior layer of breathable material having an interior layer of material in a particular treatment area, wherein the second layer of material is impregnated with a wax-based treatment. Alternatively, for direct application to the finger or toe tips, a finger/toe tip glove is provided, the finger/toe tip glove comprises a single layer of breathable material, covering only the finger or toe extremity, having a second layer of material in a particular treatment area, wherein the second layer of material is impregnated with a wax-based preparation.

A method for treating damaged areas of skin and promoting nail growth is also presented. The method comprises the steps of providing a manicure/pedicure glove comprising a single layer of breathable material having a second layer of material in a particular treatment area, wherein the second layer is impregnated with a wax-based treatment; inserting a hand or foot into the manicure/pedicure glove; and wearing the manicure/pedicure glove for a sufficient period to permit the wax-based preparation to penetrate into the treatment area.

In the preferred embodiment, the wax-impregnated treatment medium may comprise juices or oils for stimulating nail growth or softening cuticles. The juices or oils may include one or more selected from the following: lemon, carrot, lavender, grapefruit, eucalyptus, rosemary, peppermint, jojoba, evening primrose, borage, apricot kernel, almond, grape seed and avocado. The wax-impregnated treatment may also include oils for treating nail infections selected from one of the following: tea tree, thyme, eucalyptus, reaversara, radiate, myrrh, lavender, patchouli, oregano and calendula. The wax-impregnated treatment may also include a hard skin preventative such as palma rose, lemon, thyme linalool and benzoin. Other medicinal creams such as steroids may be included in the wax-impregnated treatment.

Additional objects and advantages of the invention will be set forth in part in the description which follows, and in part will be obvious from the description, or may be learned by practice of the invention. The objects and advantages of the invention will be obtained by means of instrumentalities in combinations particularly pointed out in the appended claims.

BRIEF DESCRIPTION OF THE DRAWINGS

The accompanying drawings illustrate a complete embodiment of the invention according to the best modes so far devised for the practical application of the principles thereof, and in which.

DETAILED DESCRIPTION OF THE INVENTION

Figure 1:
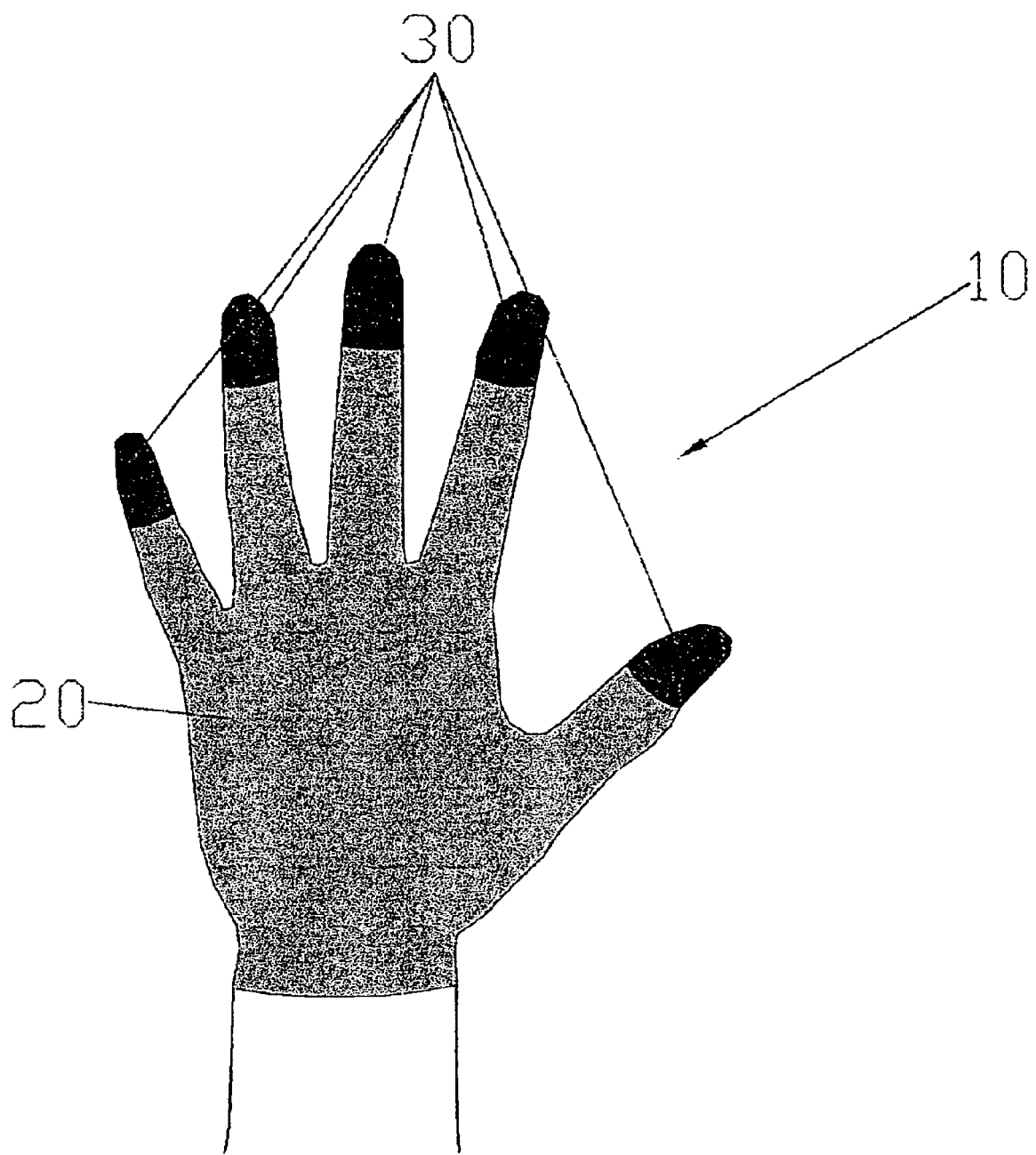
FIG. 1 is perspective view of a manicure glove of the present invention.
Figure 2:
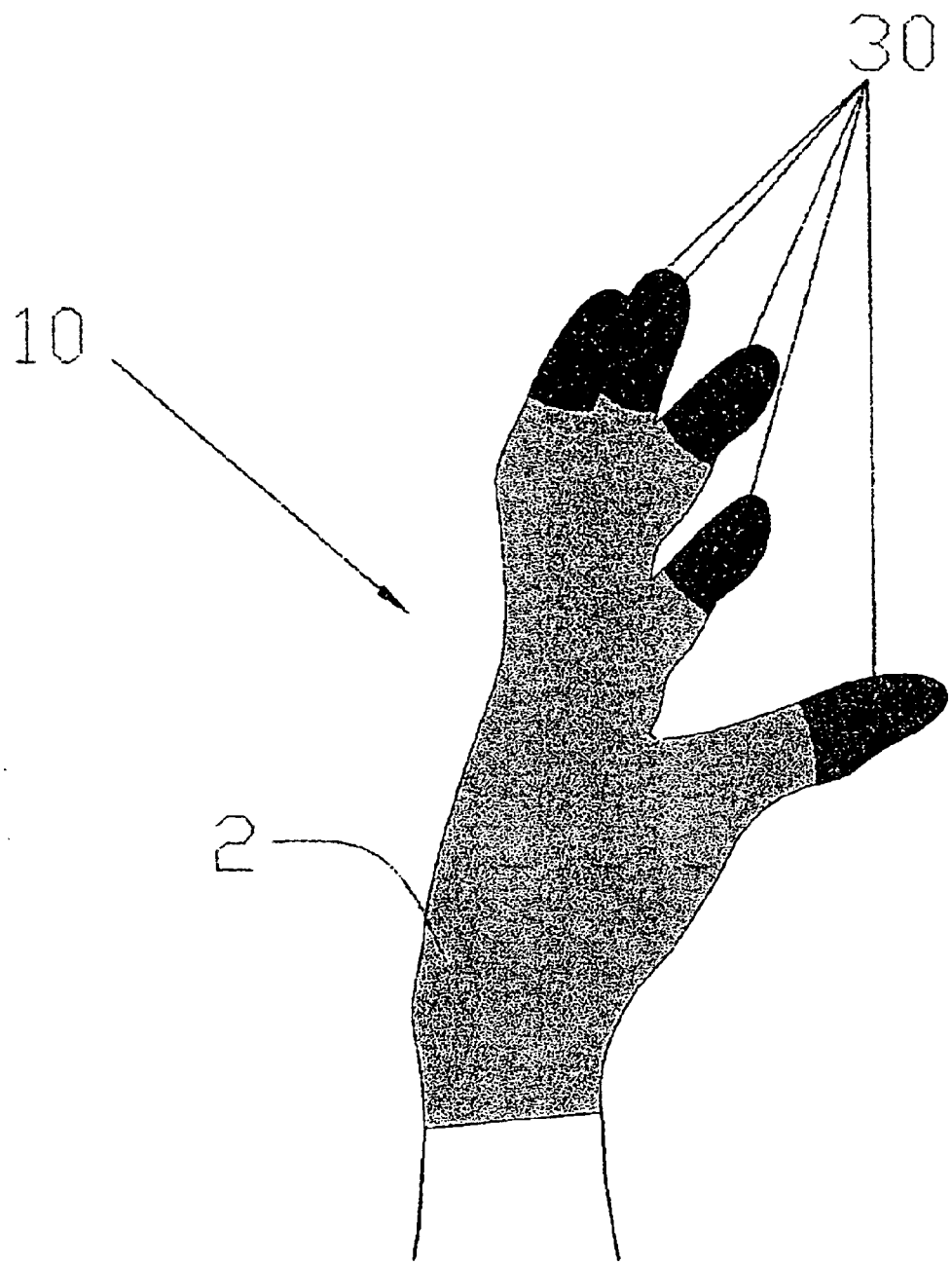
FIG. 2 is a side view of a manicure glove of the present invention.

Referring now to the drawings where similar elements are labeled the same throughout, FIGS. 1 and 2 depict a manicure glove 10 of the present invention. The glove 10 comprises of a single exterior layer 20 of breathable material. Examples of this type of material are, but are not limited to: silk, cotton, and a polymeric fiber mesh such as nylon or polyester. A second or interior layer 30 of material is positioned or deposited in the desired area of treatment. The figure depicts the preferred embodiment where the interior layer 30 of material is positioned at the finger tip and, in particular, at the finger nail and cuticle. Alternatively, the second layer of material could be positioned on the palm or between the fingers. The second layer of material is preferably a woven material capable of being impregnated with a wax-based preparation. The wax-based treatment is formulated to treat the affected area and/or to promote nail growth.

Figure 3:
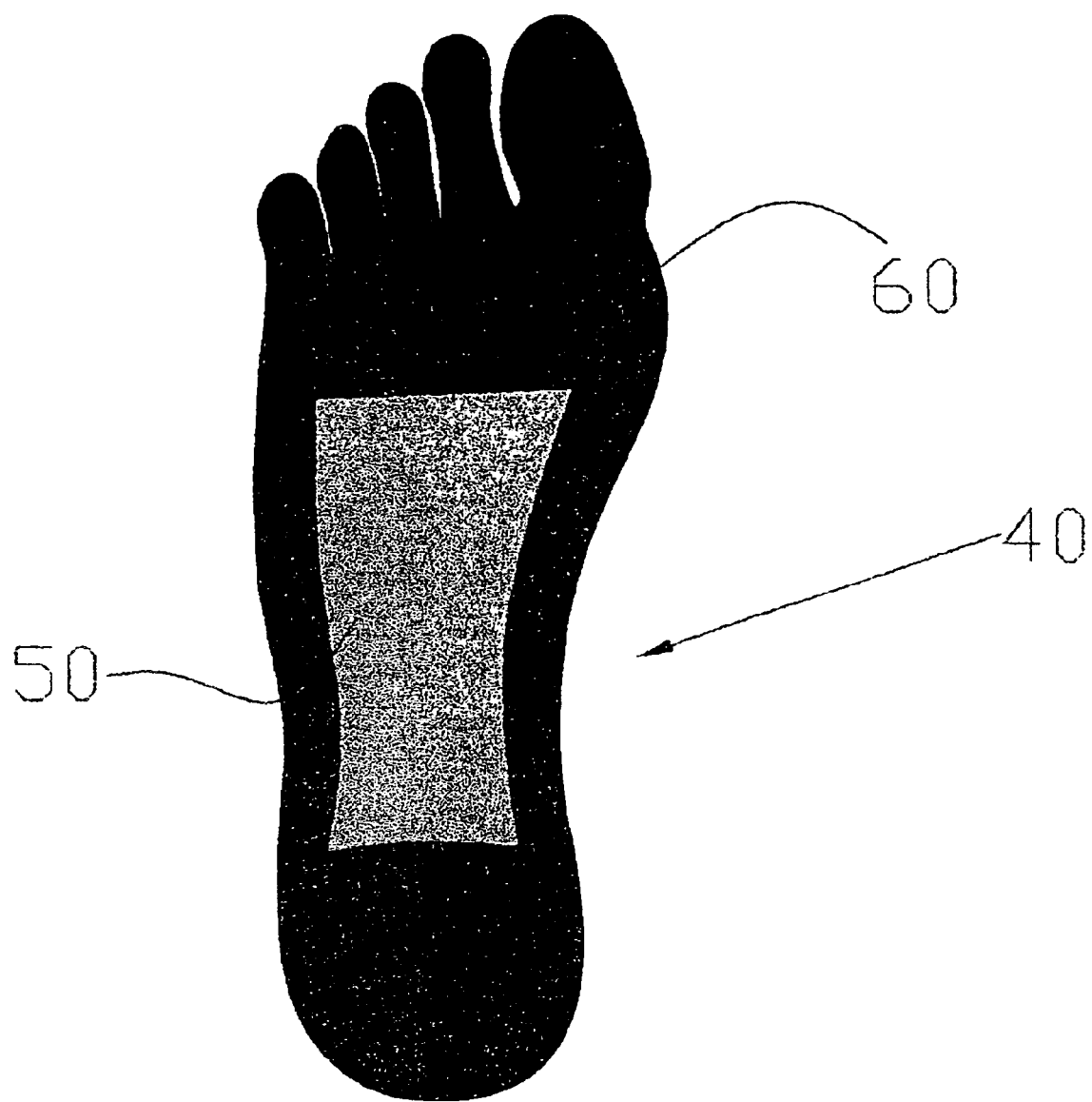
FIG. 3 is a perspective view of a pedicure glove of the present invention.
Figure 4:
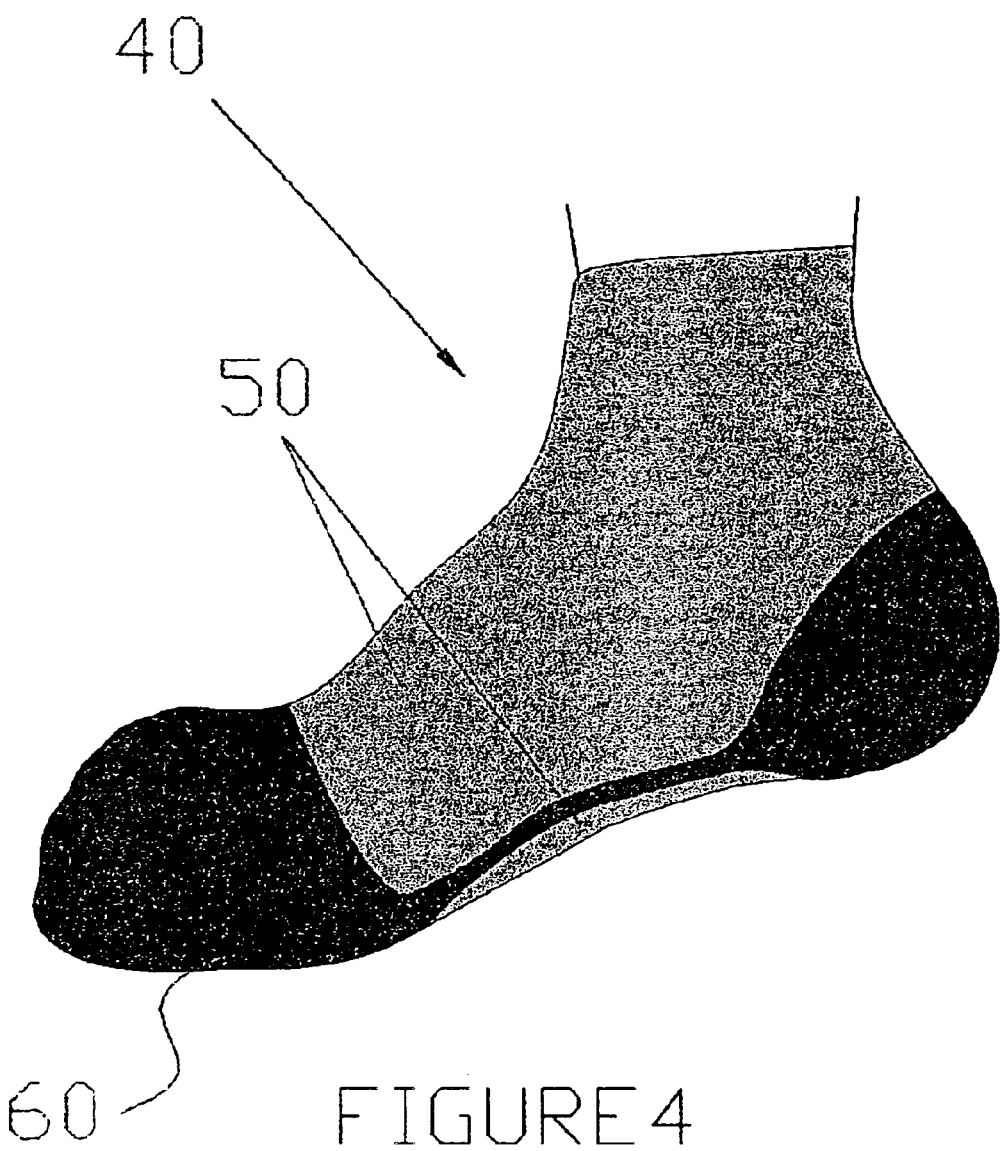
FIG. 4 is a side view of a pedicure glove of the present invention.

FIGS. 3 and 4 depict a pedicure glove 40 of the present invention. The pedicure glove 40 is similar in construction to the manicure glove. The pedicure glove 40 includes an exterior layer 50 of breathable material. Examples of this type of material are, but are not limited to: silk, cotton, nylon and a polymeric fiber mesh such as nylon or polyester. A second or interior layer 60 of material is positioned in the desired area of treatment. These figures depict a preferred embodiment where the second layer 60 of material is positioned at the ball and toes of the foot; along the sides of the sole of the foot; and at the heel of the foot.

Alternatively, the second layer of material could be positioned on the top of the foot at the toe portion to treat the cuticles and/or to enhance nail growth. The second layer of material is preferably a woven material capable of being impregnated with a wax-based preparation. The wax-based preparation is formulated to treat the affected area and/or to enhance nail growth. In the instances of the manicure and/or pedicure gloves, there may or may not be a barrier layer to prevent treatment leakage. The barrier could either be a thin plastic film between the aforementioned interior and exterior layers, or an exterior coating over the treatment areas of the glove.

The manicure/pedicure glove of the present invention may or may not be disposable. Preferably, the glove is disposable to keep risks associated with unsanitary conditions to a minimum.

The manicure/pedicure glove of the present invention is used for treating damaged areas of skin, for preventing damage to the skin, and/or for enhancing nail growth. In use, the glove is provided. A hand or foot is inserted into the glove. The glove is worn for a sufficient period to permit the wax-based preparation to penetrate into the damaged or treatment areas to repair damaged tissue and/or to enhance nail growth. The manicure glove may be worn at night or during the day, whichever time is best suitable for the user.

Figure 5:
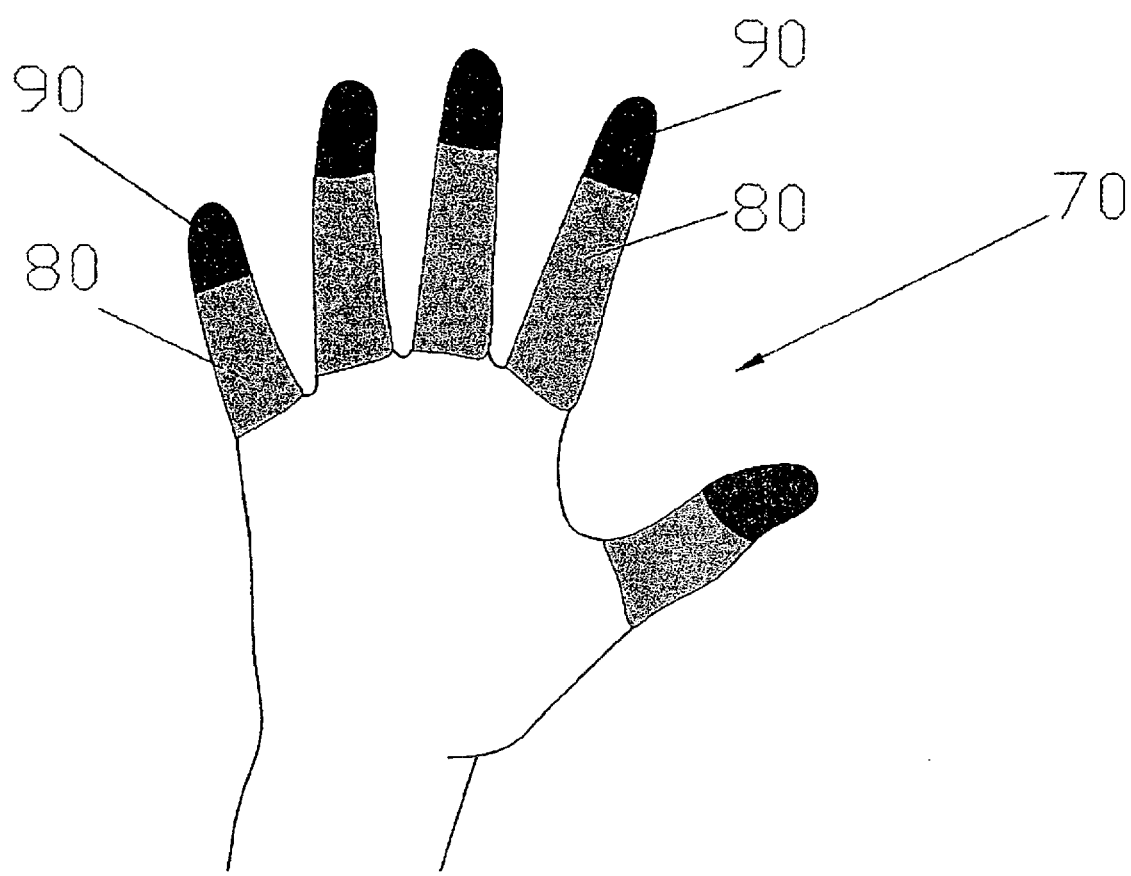
FIG. 5 depicts an alternative embodiment where only the finger or toe tip is treated.

Alternatively, one may desire not to wear a full glove but only the tips of the glove. FIG. 5 depicts an alternative embodiment of the invention where only the glove tip 70 is worn. In this case, the glove tip is worn only over either the finger or the toe and not the complete hand or foot. This application is preferred when damage may only have been done to one or two fingers/toes and a full glove application is not necessary. The finger/toe tip glove 70 comprises a single layer of breathable material 80, covering only the finger or toe extremity, having a second layer of material 90 in a particular treatment area, wherein the second layer of material 90 is impregnated with a wax-based preparation (not shown). This alternative embodiment of the invention may or may not have the same leakage precautions as the aforementioned gloves.

The glove of the present invention affords certain advantages over those of the prior art. For example, the use of a single layer breathable material eliminates the generation of sweat by the hand or foot. This reduces the chance of the glove causing other skin irritations. Also, because the second layer of material is positioned in a particular treatment area, the glove is not bulky and may be worn under other gloves or socks. The wax-based preparation eliminates the need for an outer glove layer that would otherwise need to be impenetrable to oils or lotions. Because of the wax consistency of the preparation, there less problems of migration of the preparation out of the second layer of material, especially in the instances protected with the barriers over the specific treatment areas. Rather, the woven second layer entraps the wax-based preparation causing it not to be released until it is softened at human body temperatures (98.6° F.). Thus, heat generated by the skin on the body part to be treated causes the oils, juices, moisturizers, lubricants or medicinal creams to be liberated from the wax-based preparation and allows these therapeutic materials to treat the skin in contact therewith. Storage at room temperature will not cause migration of the preparation out of the second layer of material because it is incapable of flowing until it is exposed to the softening temperature of the wax. This eliminates the need to use an outer glove shell to protect the preparation from damaging surrounding areas such as bed sheets or clothing.

The above description and drawings are only illustrative of preferred embodiments which achieve the objects, features and advantages of the present invention, and it is not intended that the present invention be limited thereto. Any modification of the present invention which comes within the spirit and scope of the following claims is considered part of the present invention. Thus, it is to be understood that the invention is not limited to the exact construction illustrated and described above, but that various changes and modifications may be made without departing from the spirit and scope of the as defined by the following claims.

I claim:

1. An applicator for delivering a dermal treatment comprising an exterior layer of breathable material surrounding an interior layer of material impregnated with a wax-based treatment and a third layer comprised of a thin plastic film that prevents leakage between said interior and exterior layers.

2. The applicator of claim 1 wherein said wax-based treatment includes one or more selected from the following: lemon, carrot, lavender, grapefruit, eucalyptus, rosemary, peppermint, jojoba, evening primrose, borage, apricot kernel, almond, grape seed and avocado.

3. The applicator of claim 1 wherein said wax-based treatment includes one or more oils for treating nail infections selected from the following: tea tree, thyme, eucalyptus, reaversara, radiate, myrrh, lavender, patchouli, oregano and calendula.

4. The applicator of claim 1 wherein said wax-based treatment includes a hard skin preventative selected from the following: palma rose, lemon, thyme linalool and benzoin.

5. A manicure/pedicure glove comprising: an exterior layer of breathable material having an interior layer of material in a particular treatment area, wherein the interior layer of material is impregnated with a wax-based preparation, and a third layer comprised of a thin plastic film that prevents leakage between said interior and exterior layers.

6. The manicure/pedicure glove according to claim 5, wherein the exterior layer of breathable material is selected from the group consisting of: silk, cotton, nylon and a polymeric fiber mesh.

7. The manicure/pedicure glove according to claim 5, wherein the interior layer of material comprises a woven material, cotton or other absorbing material.

8. The manicure/pedicure glove according to claim 5, wherein the treatment area is selected from the group consisting of: a finger tip; a finger nail; a toe nail; a heel; a foot sole; and a toe tip.

9. The manicure/pedicure glove according to claim 5, wherein the manicure/pedicure glove is disposable.

10. The manicure/pedicure glove of claim 5 wherein said wax-based preparation includes wax that is pliable at room temperature, said wax becoming soft and more viscous and releases moisturizers, lubricants or medicinal materials when the wax reaches approximately 100° F.

11. The manicure/pedicure glove of claim 5 further comprising an exterior coating covering the outside of the exterior layer.

12. A method for treating damaged areas of skin and/or enhancing nail growth, the method comprising the steps of:

a) providing a manicure/pedicure glove comprising a first layer of breathable material having a second layer of material in a particular treatment area, wherein the second layer of material is impregnated with a wax-based preparation, and a third layer comprised of a thin plastic film that prevents leakage between the first and second layers, said third layer being disposed between the first and second layers;

b) inserting a hand or foot into the manicure/pedicure glove; and c) wearing the manicure/pedicure glove for a sufficient period to permit the wax-based preparation to penetrate into the treatment area.

13. The method according to claim 12, further comprising the step of removing the manicure/pedicure glove after the wax-based preparation has penetrated into the treatment area.

14. The method of claim 12, further comprising softening said wax with body heat from the hand or foot to release moisturizers, lubricants or medicinal materials.

* * * * *